United States Patent
Shipp (10) Patent No.: US 10,098,634 B2
(45) Date of Patent: *Oct. 16, 2018

(54) ABSORBABLE FASTENER FOR HERNIA MESH FIXATION

(71) Applicant: Covidien LP, Mansfield, MA (US)

(72) Inventor: John I. Shipp, Atlantic Beach, FL (US)

(73) Assignee: Covidien LP, Mansfield, MA (US)

( * ) Notice: Subject to any disclaimer, the term of this patent is extended or adjusted under 35 U.S.C. 154(b) by 199 days.

This patent is subject to a terminal disclaimer.

(21) Appl. No.: 14/920,247

(22) Filed: Oct. 22, 2015

(65) Prior Publication Data

US 2016/0074034 A1   Mar. 17, 2016

Related U.S. Application Data

(63) Continuation of application No. 12/908,230, filed on Oct. 20, 2010, now Pat. No. 9,332,983, which is a
(Continued)

(51) Int. Cl.
*A61B 17/08*   (2006.01)
*A61B 17/064*   (2006.01)
(Continued)

(52) U.S. Cl.
CPC .......... *A61B 17/064* (2013.01); *A61B 17/068* (2013.01); *A61F 2/0063* (2013.01);
(Continued)

(58) Field of Classification Search
CPC ............ A61F 2/0063; A61F 2002/0068; A61F 2002/0072; A61F 2220/0016; A61F 2220/0041; A61B 17/128; A61B 2017/0488; A61B 17/068; A61B 17/0642; A61B 2017/0648; A61B 2017/0649; A61B 17/0487; A61B 17/08; A61B 17/083;
(Continued)

(56) References Cited

U.S. PATENT DOCUMENTS 1,757,026 A * 5/1930 Tuttle ........................ F16H 3/14
192/21
3,528,466 A * 9/1970 Tracy .................... B25B 23/065
206/338
(Continued)

FOREIGN PATENT DOCUMENTS

DE          10300787 A1    9/2004
DE     10 2010 015009 A1   10/2011
(Continued)

OTHER PUBLICATIONS

Extended European Search report corresponding to counterpart Int'l Appication No. EP 14 18 1900.3, dated Apr. 9, 2015.
(Continued)

*Primary Examiner* — Darwin Erezo
*Assistant Examiner* — Erin Colello (57) ABSTRACT

A method of forming and deploying an improved absorbable fastener for hernia mesh fixation is disclosed. The absorbable fastener of the present invention functions to securely fasten tough, non macro-porous, and relative inelastic mesh to soft tissue. The fastener is formed from co-polymers of lactide and glycolide.

19 Claims, 5 Drawing Sheets

Related U.S. Application Data continuation of application No. 11/161,702, filed on Aug. 12, 2005, which is a continuation-in-part of application No. 10/907,834, filed on Apr. 18, 2005, now Pat. No. 8,114,099, which is a continuation-in-part of application No. 10/905,020, filed on Dec. 10, 2004, now abandoned, which is a continuation-in-part of application No. 10/709,297, filed on Apr. 27, 2004, now Pat. No. 7,758,612.

(51) Int. Cl.
  *A61B 17/068* (2006.01)
  *A61F 2/00* (2006.01)
  *A61B 17/00* (2006.01)

(52) U.S. Cl.
  CPC .......... *A61B 2017/00004* (2013.01); *A61B 2017/0647* (2013.01); *A61B 2017/0648* (2013.01); *A61F 2002/0072* (2013.01); *A61F 2220/0016* (2013.01)

(58) Field of Classification Search
  CPC .......... A61B 17/10; A61B 2017/044; A61B 2017/0409; A61B 17/0401; A61B 17/105; A61B 17/861; A61B 17/86; A61B 17/064
  See application file for complete search history.

(56) References Cited

U.S. PATENT DOCUMENTS

| | | | |
|---|---|---|---|
| 3,596,528 A | 8/1971 | Dittrich et al. | |
| 3,866,510 A | 2/1975 | Eibes | |
| RE28,932 E | 8/1976 | Noiles et al. | |
| 4,350,491 A | 9/1982 | Steuer | |
| 4,884,572 A | 12/1989 | Bays et al. | |
| 5,085,661 A | 2/1992 | Moss | |
| 5,171,247 A | 12/1992 | Hughett et al. | |
| 5,171,249 A | 12/1992 | Stefanchik et al. | |
| 5,176,306 A | 1/1993 | Heimerl et al. | |
| 5,203,864 A | 4/1993 | Phillips | |
| 5,207,697 A | 5/1993 | Carusillo et al. | |
| 5,228,256 A | 7/1993 | Dreveny | |
| 5,236,563 A | 8/1993 | Loh | |
| 5,246,441 A | 9/1993 | Ross et al. | |
| 5,246,450 A | 9/1993 | Thornton et al. | |
| 5,271,543 A | 12/1993 | Grant et al. | |
| 5,290,297 A | 3/1994 | Phillips | |
| 5,312,023 A | 5/1994 | Green et al. | |
| 5,330,487 A | 7/1994 | Thornton et al. | |
| 5,344,061 A | 9/1994 | Crainich | |
| 5,356,064 A | 10/1994 | Green et al. | |
| 5,381,943 A | 1/1995 | Allen et al. | |
| 5,382,254 A | 1/1995 | McGarry et al. | |
| 5,398,861 A | 3/1995 | Green | |
| 5,403,327 A | 4/1995 | Thornton et al. | |
| 5,433,721 A | 7/1995 | Hooven et al. | |
| 5,439,468 A | 8/1995 | Schulze et al. | |
| 5,452,836 A | 9/1995 | Huitema et al. | |
| 5,466,243 A | 11/1995 | Schmieding et al. | |
| 5,467,911 A | 11/1995 | Tsuruta et al. | |
| 5,474,566 A | 12/1995 | Alesi et al. | |
| 5,474,567 A | 12/1995 | Stefanchik et al. | |
| 5,487,500 A | 1/1996 | Knodel et al. | |
| 5,522,844 A | 6/1996 | Johnson | |
| 5,527,319 A | 6/1996 | Green et al. | |
| 5,553,765 A | 9/1996 | Knodel et al. | |
| 5,562,685 A | 10/1996 | Mollenauer et al. | |
| 5,564,615 A | 10/1996 | Bishop et al. | |
| 5,582,615 A | 12/1996 | Foshee et al. | |
| 5,582,616 A * | 12/1996 | Bolduc | A61B 17/064 |
| | | | 606/139 |
| 5,584,425 A | 12/1996 | Savage et al. | |
| 5,588,581 A | 12/1996 | Conlon et al. | |
| 5,601,571 A | 2/1997 | Moss | |
| 5,601,573 A | 2/1997 | Fogelberg et al. | |
| 5,626,613 A | 5/1997 | Schmieding | |
| 5,628,752 A | 5/1997 | Asnis et al. | |
| 5,649,931 A | 7/1997 | Bryant et al. | |
| 5,662,662 A | 9/1997 | Bishop et al. | |
| 5,681,330 A | 10/1997 | Hughett et al. | |
| 5,683,401 A | 11/1997 | Schmieding et al. | |
| 5,685,474 A | 11/1997 | Seeber | |
| 5,697,935 A | 12/1997 | Moran et al. | |
| 5,709,692 A | 1/1998 | Mollenauer et al. | |
| 5,730,744 A | 3/1998 | Justin et al. | |
| 5,732,806 A | 3/1998 | Foshee et al. | |
| 5,735,854 A | 4/1998 | Caron et al. | |
| 5,741,268 A | 4/1998 | Schutz | |
| 5,762,255 A | 6/1998 | Chrisman et al. | |
| 5,782,844 A | 7/1998 | Yoon et al. | |
| 5,810,882 A | 9/1998 | Bolduc et al. | |
| 5,824,008 A | 10/1998 | Bolduc et al. | |
| 5,830,221 A * | 11/1998 | Stein | A61B 17/068 |
| | | | 606/157 |
| 5,843,087 A | 12/1998 | Jensen et al. | |
| 5,897,564 A | 4/1999 | Schulze et al. | |
| 5,904,693 A | 5/1999 | Dicesare et al. | |
| 5,910,105 A | 6/1999 | Swain et al. | |
| 5,911,722 A | 6/1999 | Adler et al. | |
| 5,928,244 A | 7/1999 | Tovey et al. | |
| 5,928,252 A | 7/1999 | Steadman et al. | |
| 5,931,844 A | 8/1999 | Thompson et al. | |
| 5,941,439 A | 8/1999 | Kammerer et al. | |
| 5,954,259 A | 9/1999 | Viola et al. | |
| 5,961,524 A | 10/1999 | Crombie | |
| 5,964,772 A | 10/1999 | Bolduc et al. | |
| 5,976,160 A | 11/1999 | Crainich | |
| 5,997,552 A | 12/1999 | Person et al. | |
| 6,010,513 A | 1/2000 | Tormala et al. | |
| 6,013,991 A | 1/2000 | Philipp | |
| 6,030,162 A * | 2/2000 | Huebner | A61B 17/1682 |
| | | | 411/263 |
| 6,039,753 A | 3/2000 | Meislin | |
| 6,074,395 A | 6/2000 | Trott et al. | |
| 6,099,537 A | 8/2000 | Sugai et al. | |
| 6,126,670 A | 10/2000 | Walker et al. | |
| 6,132,435 A | 10/2000 | Young | |
| 6,146,387 A | 11/2000 | Trott et al. | |
| 6,183,479 B1 | 2/2001 | Tormala et al. | |
| 6,228,098 B1 | 5/2001 | Kayan et al. | |
| 6,235,058 B1 | 5/2001 | Huene | |
| 6,241,736 B1 | 6/2001 | Sater et al. | |
| 6,261,302 B1 | 7/2001 | Voegele et al. | |
| 6,296,656 B1 | 10/2001 | Bolduc et al. | |
| 6,330,964 B1 | 12/2001 | Kayan et al. | |
| 6,387,113 B1 | 5/2002 | Hawkins et al. | |
| 6,402,757 B1 | 6/2002 | Moore, III et al. | |
| 6,425,900 B1 | 7/2002 | Knodel et al. | |
| 6,439,446 B1 | 8/2002 | Perry et al. | |
| 6,440,136 B1 | 8/2002 | Gambale et al. | |
| 6,447,524 B1 | 9/2002 | Knodel et al. | |
| 6,450,391 B1 | 9/2002 | Kayan et al. | |
| 6,457,625 B1 | 10/2002 | Tormala et al. | |
| 6,517,542 B1 * | 2/2003 | Papay | A61B 17/0401 |
| | | | 606/232 |
| 6,551,333 B2 | 4/2003 | Kuhns et al. | |
| 6,562,051 B1 | 5/2003 | Bolduc et al. | |
| 6,572,626 B1 | 6/2003 | Knodel et al. | |
| 6,589,249 B2 | 7/2003 | Sater et al. | |
| 6,592,593 B1 | 7/2003 | Parodi et al. | |
| 6,599,272 B1 | 7/2003 | Hjertman et al. | |
| 6,626,916 B1 | 9/2003 | Yeung et al. | |
| 6,632,228 B2 | 10/2003 | Fortier et al. | |
| 6,652,538 B2 | 11/2003 | Kayan et al. | |
| 6,663,656 B2 | 12/2003 | Schmieding et al. | |
| 6,666,854 B1 | 12/2003 | Lange | |
| 6,692,506 B1 | 2/2004 | Ory et al. | |
| 6,695,867 B2 | 2/2004 | Ginn et al. | |
| 6,733,506 B1 | 5/2004 | McDevitt et al. | |
| 6,743,240 B2 | 6/2004 | Smith et al. | |
| 6,749,621 B2 | 6/2004 | Pantages et al. | |
| 6,755,836 B1 | 6/2004 | Lewis | |
| 6,773,438 B1 | 8/2004 | Knodel et al. | |

(56) References Cited

U.S. PATENT DOCUMENTS

| | | |
|---|---|---|
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |
| 6,893,446 B2 | 5/2005 | Sater et al. |
| 6,905,057 B2 | 6/2005 | Swayze et al. |
| 6,916,333 B2* | 7/2005 | Schmieding ....... A61B 17/0401 606/232 |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,128,254 B2 | 10/2006 | Shelton, IV et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,371,244 B2 | 5/2008 | Chatlynne et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,637,932 B2 | 12/2009 | Bolduc et al. |
| 7,670,362 B2 | 3/2010 | Zergiebel |
| 7,758,612 B2 | 7/2010 | Shipp |
| 7,766,920 B2* | 8/2010 | Ciccone ............ A61B 17/1615 606/104 |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,034,076 B2 | 10/2011 | Criscuolo et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,343,176 B2 | 1/2013 | Criscuolo et al. |
| 8,343,184 B2 | 1/2013 | Blier |
| 8,382,778 B2 | 2/2013 | Criscuolo et al. |
| 8,414,627 B2 | 4/2013 | Corradi et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,685,044 B2 | 4/2014 | Bolduc et al. |
| 8,690,897 B2 | 4/2014 | Bolduc |
| 8,728,102 B2 | 5/2014 | Criscuolo et al. |
| 8,728,120 B2 | 5/2014 | Blier |
| 8,777,969 B2* | 7/2014 | Kayan ................ A61B 17/064 411/386 |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,920,439 B2 | 12/2014 | Cardinale et al. |
| 8,926,637 B2 | 1/2015 | Zergiebel |
| 8,968,311 B2 | 3/2015 | Allen, IV et al. |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,274 B2 | 6/2016 | Zergiebel |
| 9,402,623 B2 | 8/2016 | Kayan |
| 9,486,218 B2 | 11/2016 | Criscuolo et al. |
| 9,526,498 B2 | 12/2016 | Reed |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,801,633 B2 | 10/2017 | Sholev et al. |
| 9,867,620 B2 | 1/2018 | Fischvogt et al. |
| 2002/0068947 A1 | 6/2002 | Kuhns et al. |
| 2003/0009441 A1 | 1/2003 | Holsten et al. |
| 2003/0114839 A1 | 6/2003 | Looper et al. |
| 2004/0092937 A1 | 5/2004 | Criscuolo et al. |
| 2004/0111089 A1 | 6/2004 | Stevens et al. |
| 2004/0127916 A1 | 7/2004 | Bolduc et al. |
| 2004/0181222 A1 | 9/2004 | Culbert et al. |
| 2004/0193217 A1 | 9/2004 | Lubbers et al. |
| 2004/0204723 A1* | 10/2004 | Kayan .................. A61B 17/064 606/151 |
| 2004/0243139 A1* | 12/2004 | Lewis ................ A61B 17/862 606/104 |
| 2005/0070904 A1* | 3/2005 | Gerlach ............ A61B 17/8014 606/281 |
| 2005/0070958 A1 | 3/2005 | Swayze et al. |
| 2005/0149031 A1* | 7/2005 | Ciccone ............ A61B 17/1615 606/280 |
| 2005/0171562 A1* | 8/2005 | Criscuolo ............ A61B 17/064 606/151 |
| 2005/0267478 A1 | 12/2005 | Corradi et al. |
| 2006/0100629 A1 | 5/2006 | Lee |
| 2006/0129152 A1 | 6/2006 | Shipp |
| 2006/0129154 A1 | 6/2006 | Shipp |
| 2006/0241622 A1* | 10/2006 | Zergiebel ............. A61B 17/064 606/916 |
| 2007/0038220 A1 | 2/2007 | Shipp |
| 2007/0088390 A1 | 4/2007 | Paz et al. |
| 2007/0162030 A1 | 7/2007 | Aranyi et al. |
| 2008/0086154 A1 | 4/2008 | Taylor et al. |
| 2008/0097523 A1 | 4/2008 | Bolduc et al. |
| 2008/0147113 A1 | 6/2008 | Nobis et al. |
| 2008/0188868 A1 | 8/2008 | Weitzner et al. |
| 2008/0243106 A1 | 10/2008 | Coe et al. |
| 2008/0281336 A1 | 11/2008 | Zergiebel |
| 2008/0312687 A1 | 12/2008 | Blier |
| 2009/0112234 A1 | 4/2009 | Crainich et al. |
| 2009/0118776 A1 | 5/2009 | Kelsch et al. |
| 2009/0188965 A1 | 7/2009 | Levin et al. |
| 2010/0030262 A1 | 2/2010 | McLean et al. |
| 2010/0270354 A1 | 10/2010 | Rimer et al. |
| 2010/0292710 A1 | 11/2010 | Daniel et al. |
| 2010/0292713 A1 | 11/2010 | Cohn et al. |
| 2010/0292715 A1 | 11/2010 | Nering et al. |
| 2011/0022065 A1 | 1/2011 | Shipp |
| 2011/0042441 A1 | 2/2011 | Shelton, IV et al. |
| 2011/0060349 A1 | 3/2011 | Cheng et al. |
| 2011/0071578 A1 | 3/2011 | Colesanti et al. |
| 2011/0079627 A1 | 4/2011 | Cardinale et al. |
| 2011/0087240 A1 | 4/2011 | Shipp |
| 2011/0204120 A1 | 8/2011 | Crainich |
| 2011/0295269 A1 | 12/2011 | Swensgard et al. |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2013/0018392 A1 | 1/2013 | Zergiebel |

(56) References Cited

U.S. PATENT DOCUMENTS

| | | |
|---|---|---|
| 2013/0110088 A1 | 5/2013 | Wenchell |
| 2013/0131700 A1 | 5/2013 | Criscuolo et al. |
| 2013/0197591 A1 | 8/2013 | Corradi et al. |
| 2014/0114329 A1 | 4/2014 | Zergiebel |
| 2014/0121684 A1 | 5/2014 | Criscuolo et al. |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0018847 A1 | 1/2015 | Criscuolo et al. |
| 2015/0032130 A1 | 1/2015 | Russo |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |
| 2016/0007996 A1 | 1/2016 | Bolduc |
| 2016/0066971 A1 | 3/2016 | Corradi et al. |
| 2016/0074034 A1 | 3/2016 | Shipp |
| 2016/0135807 A1 | 5/2016 | Zergiebel |
| 2016/0166255 A1 | 6/2016 | Fischvogt |
| 2016/0249912 A1 | 9/2016 | Fischvogt |
| 2016/0270778 A1 | 9/2016 | Zergiebel |
| 2016/0270835 A1 | 9/2016 | Reed |
| 2016/0278766 A1 | 9/2016 | Wenchell et al. |
| 2016/0338694 A1 | 11/2016 | Kayan |
| 2016/0345967 A1 | 12/2016 | Sniffin et al. |
| 2017/0042657 A1 | 2/2017 | Criscuolo et al. |
| 2017/0128068 A1 | 5/2017 | Zhang et al. |
| 2017/0151048 A1 | 6/2017 | Russo |
| 2017/0231631 A1 | 8/2017 | Abuzaina et al. |
| 2017/0265859 A1 | 9/2017 | Sniffin et al. |
| 2018/0042591 A1 | 2/2018 | Russo et al. |

FOREIGN PATENT DOCUMENTS

| | | |
|---|---|---|
| EP | 0374088 A1 | 6/1990 |
| EP | 0834280 A1 | 4/1998 |
| EP | 1273272 A2 | 1/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| EP | 2853202 A2 | 4/2015 |
| JP | 09149906 | 6/1997 |
| WO | 00/16701 A1 | 3/2000 |
| WO | 2002/034140 A2 | 5/2002 |
| WO | 2003/034925 A2 | 5/2003 |
| WO | 2003/103507 A2 | 12/2003 |
| WO | 2004/112841 A2 | 12/2004 |
| WO | 2005004727 A1 | 1/2005 |
| WO | 2009/039506 A1 | 3/2009 |
| WO | 2012/064692 A2 | 5/2012 |
| WO | 2013/046115 A1 | 4/2013 |

OTHER PUBLICATIONS

Extended European Search report corresponding to counterpart Int'l Appication No. EP 14 19 7885.8, dated Apr. 30, 2015.
Extended European Search Report corresponding to counterpart application EP 10 01 2659.8, completed Dec. 21, 2010 and dated Jan. 3, 2011; 3 pages.
Extended European Search Report corresponding to counterpart application EP 10 01 2646.5, completed Feb. 11, 2011 and dated Feb. 22, 2011; 10 pages.
Extended European Search Report corresponding to counterpart application EP 11 25 0549.0, completed Sep. 9, 2013 and dated Sep. 17, 2013; 9 pages.
Extended European Search Report corresponding to counterpart application EP 14 15 9394.7, completed Apr. 16, 2014 and dated Apr. 29, 2014; 8 pages.
Extended European Search Report corresponding to counterpart application EP 14 15 8946.5, completed Jun. 20, 2014 and dated Jul. 8, 2014; (9 pp).
Extended European Search Report corresponding to counterpart application EP 14 17 8107.0, completed Nov. 24, 2014 and dated Dec. 3, 2014; (5 pp).
Extended European Search Report corresponding to counterpart application EP 14 17 4656.0, completed Jan. 16, 2015 and dated Jan. 26, 2015; (7 pp).
Extended European Search Report corresponding to counterpart application EP 14 18 4907.5, completed Jan. 12, 2015 and dated Jan. 27, 2015; (9 pp).
Extended European Search Report corresponding to counterpart Int'l Appln. No. EP 14 81 7036.8 dated Feb. 2, 2017.
European Office Action corresponding to counterpart Int'l Appln. No. EP 14 19 7885.8 dated Feb. 7, 2017.
Chinese First Office Action corresponding to counterpart Int'l Appln. No. CN 201410090675 dated Feb. 28, 2017.
Extended European Search Report corresponding to counterpart Int'l Appln. No. EP 16 19 8333.3 dated Mar. 15, 2017.
European Office Action corresponding to counterpart Int'l Appln. No. EP 14 15 1663.3 dated May 10, 2017.
Extended European Search Report corresponding to counterpart Int'l Appln. No. EP 17 15 7259.7 dated May 10, 2017.
Chinese First Office Action corresponding to counterpart Int'l Appln. No. CN 2014103559671 dated Jun. 13, 2017.
Australian Examination Report No. 1 corresponding to counterpart Int'l Appln. No. AU 2014200071 dated Jun. 20, 2017.
Australian Examination Report No. 1 corresponding to counterpart Int'l Appln. No. AU 2014201338 dated Jul. 10, 2017.
Extended European Search Report corresponding to Int'l Application No. EP 14 15 1663.3 dated Jun. 7, 2016.
Chinese First Office Action corresponding to Chinese Patent Appln. No. 201480037169.2 dated Jun. 29, 2017.
Chinese First Office Action corresponding to Chinese Patent Appln. No. 201410418879.1 dated Jun. 29, 2017.
European Office Action corresponding to European Patent Appln. No. 14 17 8107.0 dated Oct. 12, 2017.
Australian Examination Report No. 1 corresponding to Australian Patent Appln. No. 2014200870 dated Oct. 26, 2017.
Chinese Second Office Action corresponding to Chinese Patent Appln. No. 201410090675 dated Nov. 6, 2017.
Japanese Office Action corresponding to Japanese Patent Appln. No. 2014-048652 dated Nov. 14, 2017.
Japanese Office Action corresponding to Japanese Patent Appln. No. 2014-047708 dated Nov. 14, 2017.
Chinese Second Office Action corresponding to Chinese Patent Appln. No. 2014103063407 dated Feb. 1, 2018.
Australian Examination Report No. 1 corresponding to Australian Patent Appln. No. 2014202970 dated Mar. 9, 2018.
Japanese Office Action corresponding to Japanese Patent Appln. No. 2014-048652 dated Mar. 15, 2018.
Chinese Second Office Action corresponding to Chinese Patent Appln. No. 201480077682.4 dated Mar. 21, 2018.
Australian Examination Report No. 1 corresponding to Australian Patent Appln. No. 2014202972 dated Mar. 27, 2018.

* cited by examiner

ABSORBABLE FASTENER FOR HERNIA MESH FIXATION

CROSS-REFERENCE TO RELATED APPLICATIONS

The present application is a continuation of U.S. patent application Ser. No. 12/908,230, filed Oct. 20, 2010, now U.S. Pat. No. 9,332,983, which is a Continuation application claiming the benefit of and priority to U.S. patent application Ser. No. 11/161,702, filed on Aug. 12, 2005, which is a Continuation-in-Part Application claiming the benefit of and priority to U.S. patent application Ser. No. 10/907,834, filed on Apr. 18, 2005 (now U.S. Pat. No. 8,114,099), which is a Continuation-in-Part application claiming the benefit of and priority to U.S. patent application Ser. No. 10/905,020, filed on Dec. 10, 2004 (now abandoned), which is a Continuation-in-Part Application claiming the benefit of and priority to U.S. patent application Ser. No. 10/709,297, filed on Apr. 27, 2004 (now U.S. Pat. No. 7,758,612), the entire contents of each of which is incorporated by reference herein.

BACKGROUND

Technical Field

This invention relates to surgical fasteners and their associated applicators, and more particularly, surgically fastening material to tissue and their method of use.

In laparoscopic repair of hernia fasteners have been used to attach repair mesh over the hernia defect so that bowel and other abdominal tissue are blocked from forming an external bulge that is typical of abdominal hernias. The role of the fasteners is to keep the mesh in proper position until tissue ingrowth is adequate to hold the mesh in place under various internal and external conditions. Adequate ingrowth usually takes place in 6-8 weeks. After that time the fasteners play no therapeutic role. Fixation fasteners comprise a mesh fixation feature, or head, a mesh-tissue interface section, and a tissue-snaring feature that holds the fastener in place under force developed inside or outside the body.

At present, there are a variety of surgical devices and fasteners available for the surgeon to use in endoscopic and open procedures to attach the mesh patch to the inguinal floor or abdominal wall. One such mesh attachment instrument uses a helical wire fastener formed in the shape of a helical compression spring. Multiple helical wire fasteners are stored serially within the 5 mm shaft, and are screwed or rotated into the mesh and the overlaid tissue to form the fastener for the prosthesis. A load spring is used to bias or feed the plurality of helical fasteners distally within the shaft. A protrusion extends into the shaft, while preventing the ejection of the stack of fasteners by the load spring, allows passage of the rotating fastener. U.S. Pat. Nos. 5,582,616 and 5,810,882 by Lee Bolduc, and U.S. Pat. No. 5,830,221 by Jeffrey Stein describe instruments and fasteners of this type.

U.S. Pat. Nos. 5,203,864 and 5,290,297 by Phillips describe two embodiments of a hernia fastener and delivery devices. One of the Phillips fasteners is formed in the shape of a unidirectional dart with flexible anchor members. The dart is forced through the mesh and into tissue by a drive rod urged distally by the surgeon's thumb. The anchor members are forced inward until the distal end of the dart penetrates the overlaid tissue and then the anchor members, presumably, expand outward without any proximal force on the dart thus forming an anchor arrangement. This requires an extremely forceful spring force generated by the anchor members. Multiple darts are stored in a rotating cylinder, much like a revolver handgun.

Phillips second fastener embodiment is a flexible H shaped device. The tissue penetrating means is a hollow needle containing one of the legs of the H. The H shape is flattened with the cross member and the other leg remaining outside the hollow needle owing to a longitudinal slot therein. A drive rod urged distally by the surgeon's thumb again delivers the fastener. The contained leg of the H penetrates the mesh and tissue. After ejection the fastener presumably returns to the equilibrium H shape with one leg below the tissue and one leg in contact with the mesh with the cross member penetrating the mesh and the tissue, similar to some plastic clothing tag attachments. Phillips depicts the installed device returning to the H shape but he fails to teach how to generate enough spring action from the device to overcome the high radial forces generated by the tissue.

A series of U.S. Pat. Nos. 6,572,626, 6,551,333, 6,447,524, and 6,425,900 and patent applications 200200877170 and 20020068947 by Kuhns and Kodel, all assigned to Ethicon, describe super elastic, or shape metal fasteners and a delivery mechanism for them. The fasteners are stored in the delivery device in a smaller state and upon insertion into the mesh and tissue, transitions to a larger anchor shaped state. The Ethicon fastener is delivered by an elaborate multistage mechanism through a hollow needle that has penetrated the mesh and the tissue. The hollow needle is then retracted to leave the fastener to change shape to a more suitable configuration for holding the mesh in place.

The primary problem associated with metallic fasteners is the formulation of permanent adhesions that attach themselves to the metallic implant. These adhesions can be of such a severity that fistulas are sometimes known to form and fasteners have been reported to migrate into the bowl and bladder. According to Joels and others, in Surg Endosc (2005) 19: 780-785, adhesions form on titanium abdominal implants and more severely on shape metal implants.

Another major problem with these prior art fasteners is that the mesh is attached to body tissue in as many as 100 places for large ventral hernias. This results in a large quantity of metal remaining in the body as permanent implants, even though after the ingrowth phase the fasteners serve no useful purpose. Compounding this problem the distal ends of the fasteners are sharp pointed and thus pose a continued pain or nerve damage hazard.

One alternative to metallic fixation devices is bio-absorbable materials. These materials are degraded in the body by hydrolysis. This precludes permanent pain sites and minimizes or eliminates adhesions since after degradation the body metabolizes them as carbon dioxide and water. These materials require special attention to many design details, however, that is much more demanding than their counterparts in metallic fixation devices such as applicator tool design, sterilization processes, and packaging. Metallic tacks or fasteners provide structural strength that simplifies their insertion and since the materials, usually titanium or nickel-titanium alloys (shape metal), are chemical and radiation resistant and are very temperature tolerant many options are available to the designer that are not available for bio-absorbable materials.

The basic considerations of an effective mesh fixation applicator and absorbable fastener are the material strength, absorption time, the sterilization method, and packaging requirements, the ease of insertion of the fastener through the mesh and into the tissue, the ease of ejecting the fastener from the tool, the fixation strength of the fastener once implanted, the time required after insertion for the fastener to be degraded and metabolized by the body are all effected by the choice of fastener material, the geometry of the design, and the forming process.

Materials of appropriate strength are generally limited to synthetic materials. Currently, the U.S. FDA has cleared devices made from polyglycolide (PG), polylactide (PL), poly caprolactone, poly dioxanone, trimethylene carbonate, and some of their co-polymers for implant in the human body. These materials and their co-polymers exhibit a wide variation of properties. Flex modulus ranges from a few thousand to a few million PSI, tensile strength ranges from 1000 to 20,000 PSI, in vivo absorption times range from a few days to more than two years, glass transition temperatures range from 30-65 degrees centigrade, all with acceptable bio-responses. Unfortunately, however, the optimum values of each of these properties are not available in any one of these materials so that it is necessary to make performance tradeoffs.

Mechanical Properties

Most hernia mesh fixation devices are currently used in laparoscopic hernia repair. In general laparoscopic entry ports have been standardized to either 5 or 10 mm (nominal) diameter. In the case of prior art of metallic fixation devices 5 mm applicators are universally employed. Since it is not clear that the medical advantages of the use of absorbable fasteners would totally out weigh the disadvantages of moving to a 10 mm applicator it must be assumed that absorbable fasteners must also employ 5 mm applicators. Because of the lower strength of absorbable material this requirement imposes severe design constraints on both the applier and the fastener.

Implanted mesh fasteners are subjected to pull out forces from a number of sources. Non-porous mesh can be subjected to forces perpendicular to the abdominal wall by interabdominal pressure increases such as experienced during sneezing or coughing. These increased forces on the mesh are rather small however and non-existent for porous mesh. Most meshes in use today have a tendency to shrink after implant. The forces resulting from the shrinkage is, primarily, parallel to the abdominal surface and results in high shear and tensile forces on the fasteners. These forces can result in fixation failure. The fastener can fracture, separating the mesh holding feature from the tissue-snaring feature or it can pull out of the tissue owing to inadequate tissue snaring. Alternately, helical wire fasteners can unwind and offer little resistance to pull out. The shape metal anchor is inserted through a large needle hole and since it is flexible and very narrow in one dimension it can separate from the mesh owing to the mesh anchor arms bending upwards and threading back through the large insertion hole. The anchor often remains lodged in the tissue while separating from the mesh in this manner.

The strength and flexibility of the fastener material are of major importance in the design considerations of the applicator, particularly in the case of fasteners formed from polymers. Ory, et al (U.S. Pat. No. 6,692,506) teaches the use of L Lactic Acid polymer. Ory discloses adequate fixation strengths but the applicator device required to insert his fastener is necessarily 10 mm in diameter thereby causing the procedure to be more invasive than necessary. Ory further discloses a hollow needle with a large outside diameter, through which the fastener is inserted, that forms a rather large hole in the mesh and tissue to supply adequate columnar strength for penetration of the fastener. Entry holes of this size can give rise to multiple small hernias know as Swiss cheese hernias.

Absorption Time

There are two forms of PL, one synthesized from the d optical isomer and the other from the l optical isomer. These are sometimes designated DPL and LPL. A polymer with 50-50 random mixture of L and D is herein designated DLPL.

High molecular weight homo and co-polymers of PG and PL exhibit absorption times ranging from 1 month to greater than 24 months. Homo crystalline PG and PL generally require greater than 6 months to absorb and thus are not optimum materials for hernia mesh fixation. Amorphous co-polymers of PG and PL, on the other hand, typically degrade in less than 6 months and are preferably used in the present invention. For high molecular weight co-polymers of PG and PL the actual absorption time is dependent on the molar ratio and the residual monomer content. For a given monomer residual the absorption time varies from about 1 month to about 5 months as the molar content of DLPL increases from 50 to 85 percent with PG decreasing from 50 to 15 percent. Co-polymers of DLPL and PG in the molar range of 50 to 85 percent of DLPL are preferred for this invention. The geometry of the fastener also effects the absorption time. Smaller high surface area devices absorb faster.

The time required for the human body to react to the foreign body of the mesh for tissue ingrowth into the mesh is typically 10 days. However, mesh migration and mesh contraction can occur for more than two months if not adequately stabilized. Since fixation fasteners can impinge upon nerves and cause pain it is desirable for the fasteners to be absorbed as soon as possible after the tissue ingrowth and after the mesh is secure against migration or contraction. For most absorbable materials there is a difference between the time for loss of fixation strength and mass loss. Fixation strength decreases quicker than fastener mass owing to some degree of crystalline structure in the polymer. For these reasons the preferred absorption time for the current invention is 3-5 months after implant.

Absorption time can be effected by radiation sterilization. This must be taken into account when formulating the polymer if radiation sterilization is to be used. For large sterilization doses polymers may have to be formulated with longer than needed absorption times prior to radiation sterilization so that the desired absorption time is obtain after sterilization since radiation, generally, tends to reduce absorption time.

Temperature Effects

Glass transition temperature (Tg) is the temperature above which a polymer becomes soft, can lose its shape, and upon re-cooling can shrink considerably. Both crystalline and amorphous polymers exhibit glass transitions in a temperature range that depends on the mobility of the molecules, which is effected by a number of factors such as molecular weight and the amount of residual monomers. Glass transition temperatures range from about 43 to 55 degrees centigrade (deg. C.) for co-polymers of PG and DLPL. Where as 100% PG has a Tg of 35-40 deg. C. and 100% PL exhibits a Tg from 50-60 deg. C. Since the core temperature of the body can reach 40 degrees C. the preferred Tg for the material comprising the current invention is greater than 40 deg. C. In addition hernia mesh fasteners are often manufactured and shipped via surface transportation under uncontrolled, extreme heat conditions. Temperatures in commercial shipping compartments in the summer can exceed 60 degrees C. It is necessary to provide thermal protection in the packaging so that the fastener temperature does not exceed its Tg.

Sterilization and Packaging

Bio-absorbable polymers degrade when exposed to high humidity and temperature. Autoclaving cannot be used, for example. Most ethylene oxide (ETO) sterilization processes employ steam and high temperatures (above Tg) to obtain reasonable "kill" times for the bio-burden commonly found on the device. High doses of gamma radiation or electron beam radiation (E Bream), both accepted methods of sterilization for many devices, could weaken the mechanical properties of PG, PL and their co-polymers. It is therefore necessary during the manufacturing process of the fastener and its applicator to maintain cleanliness to a high degree such that the bio-burden of the components is small enough so that pathogens are adequately eradicated with less severe forms of sterilization.

Radiation doses above 25 kilogray (kgy) are known to lessen the mechanical strength of bio-absorbable polymers whereas some pathogens are known to resist radiation doses below 10 kgy. It is necessary, for the preferred embodiment of the present invention, during manufacturing to keep the pathogen count below a certain threshold to insure the accepted regulatory standards are met for radiation levels between 10 and 25 kgy.

In a second embodiment of the present invention it is necessary during manufacturing to keep the pathogen count below a certain threshold to insure the accepted regulatory standards are obtained for sterilization using a non-steam, low temperature, ethylene oxide (ETO) process below Tg of the fastener polymer.

Fasteners of the present invention must be carefully packaged to maintain adequate shelf life prior to use. Care must be taken to hermetically seal the device and to either vacuum pack, flood the package with a non-reactive dry gas prior to sealing, or to pack the device with a desiccant to absorb any water vapor since hydrolysis breaks down the backbone of the co-polymers.

ETO sterilization requires the gas to contact the device to be sterilized. Devices that are not humidity sensitive can be packaged in a breathable packaging material so that ETO can diffuse in, and after sterilization, diffuse out so that the device can be sterilized without unsealing the packaging. For the alternate embodiment of the present invention the device must be hermetically sealed after sterilization with ETO. Since gamma radiation and electron beam radiation sterilization can be accomplished through hermetically sealed packaging without disturbing the seal, either of these two sterilization processes is employed for the preferred embodiment of the present invention.

Ory, et al (U.S. Pat. No. 6,692,506), Criscuolo, et al (U.S. application 20040092937), Phillips (U.S. Pat. Nos. 5,203,864 and 5,290,297), Kayan (U.S. application 20040204723), and Shipp (U.S. application Ser. Nos. 10/709,297, 10/905,020, and 10/907,834) have suggested the use of bio-absorbable materials for use as hernia mesh fixation devices to solve the problems associated with the permanency of metal implants. Ory, preferably, suggests forming the fixation device from LPL but the absorption time for LPL can exceed two years, much longer than optimum for hernia fixation devices since the lessening of pain depends on mass loss of the device. While Phillips and Kayan advocate the use of bio-absorbable material to form the fastener neither teach any details or methods for effectuating such a device. Criscuolo suggests the use of PG and PL with an absorption time of 2-3 weeks but does not disclose a method of forming the device that results in such an absorption time. In any respect, migration and contraction of the mesh has been documented to occur up to 8 weeks after implant. Loss of fixation after 2 to 3 weeks could well lead to hernia recurrence.

Hernia mesh such as PTFE based mesh manufactured by W. L. Gore is difficult to penetrate since the material is tough, non macro-porous, and relative inelastic. Attempts to penetrate these types of meshes with a puncture type applicator result in the mesh indenting into the tissue to a significant depth prior to penetration, especially for soft tissue. This indentation sometimes allows the tissue penetrator means, often a hollow needle, to penetrate through the abdomen wall and into the surgeon's hand, thus exposing the surgeon to potential hepatitis and AIDS viruses. The fastener of the present invention is equipped with screw threads that easily penetrate tough, non macro-porous, and relative inelastic mesh with a minimum of indentation. Once the threads are screwed through the mesh the underlying tissue is pull toward the mesh by the threads rather than push away from the mesh as is the case with puncture type devices.

Details of the method of manufacturing the improved fastener are herein provided.

What is needed then is an absorbable mesh fixation fastener and a method of forming an absorbable mesh fixation fastener that exhibits a known absorption time and that exhibits the mechanical properties adequate for the desired fixation strength and the required implant forces.

What is also needed is a method of packaging an absorbable mesh fixation device and the delivery device that minimizes the effects of high ambient shipping temperatures and humidity.

What is also needed is a method of sterilization of an absorbable mesh fixation fastener and its delivery device that has minimal effect on their physical properties, particularly the fastener.

What is further needed then is an absorbable mesh fixation fastener of improved geometry that easily penetrates tough, non macro-porous, and relatively inelastic mesh with minimal indentation to minimize the possibility of the fastener breaching the abdominal wall.

SUMMARY OF THE INVENTION

A method of producing and deploying a bio-absorbable hernia mesh fixation fastener exhibiting an in vivo absorption time between 1.5 and 13 months and its method of use is disclosed. A method of sterilization and a method of packaging the fastener to retain the critical physical properties of the fastener prior to implantation are also disclosed. The hernia mesh fixation device of the present invention is, preferably, injection molded using any of a variety of mole fractions of d, 1-lactide and glycolide co-polymers, depending upon the desired absorption time, and mechanical properties. Preferably the mole ratio is 75-25 percent d, 1 lactide to glycolide yielding an absorption time after implant of 4-5 months and a glass transition temperature of 49 Deg. C. The modulus of elasticity of the preferred embodiment is 192,000 PSI and the tensile strength is 7200 PSI after injection molding at 150 Deg. C.

The fastener of the present invention comprises a head with a threaded portion and a slotted portion, a truncated, threaded tissue-snaring section that, upon rotation, easily penetrates tough, non macro-porous, and relative inelastic mesh and pulls underlying tissue toward the head of the fastener, firmly anchoring the mesh to the tissue and thus avoiding excessive indentation of the abdominal wall during deployment.

The fastener deliver device, or applier, of the present invention has a longitudinal axis, a proximal body, a handle, a rotator, a fastener retainer, a fastener advancer, a force reactor, and an fastener ejector.

Sterilization standards by the U.S. FDA allow radiation doses less than 25 kgy provided the bio-burden is below 1000 colony forming units (CFU). The components of the delivery device and the fasteners of the present invention are manufactured and assembled under clean room conditions such the bio-burden is well below 1000 CFUs. This allows gamma and E Beam sterilization with doses below the damage threshold of the preferred co-polymers of DLPL and PG, 25 kgy. Mechanical properties of the injected molded fastener of the present invention have been retested after dosing with 25 kgy E Beam. The same values of flex modulus and tensile strength were measured before and after dosing. Gamma or E Beam is the preferred sterilization process, however, an alternate embodiment comprises sterilization employing ethylene oxide without the use of steam and dosed at a temperature below the glass transition temperature.

For the preferred embodiment of the present invention the delivery device loaded with fasteners is first sealed into a vacuum formed tray with a breathable Tyvek (a registered trademark of DuPont) lid. This tray is then further hermetically sealed into a foil pouch. The foil pouch is then placed inside an insulated shipping container. The insulation is adequate to assure that the temperature of the fastener remains below 30 deg. C. after exposure to severe heat conditions sometimes experienced during shipping. Gamma or E Beam sterilization is accomplished by radiation through the shipping container.

In an alternate embodiment the sealed vacuum formed tray is placed into the hermetically sealed foil pouch after ETO sterilization. The ETO will penetrate the breathable lid. After the ETO process the device is sealed into the foil pouch and the pouch is placed into the thermally insulated container described above for shipping.

DETAILED DESCRIPTION

Figure 1:
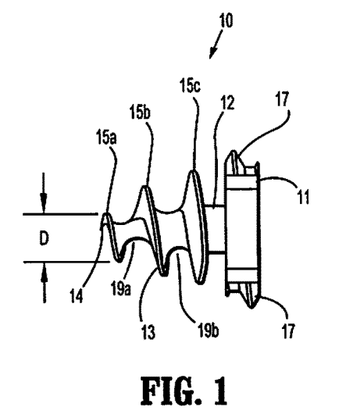
FIG. 1 is a side view of the fastener according to the present invention.
Figure 2:
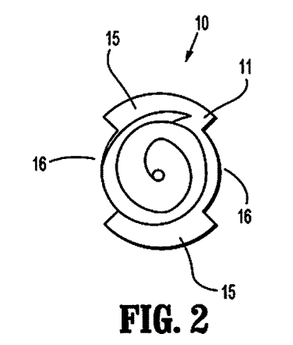
FIG. 2 is the distal end view of the fastener according to the present invention.
Figure 3:
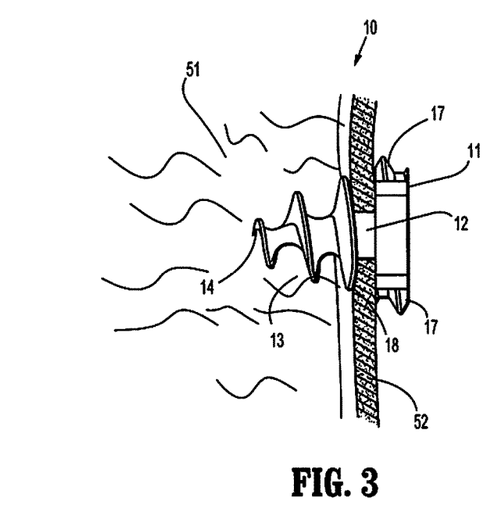
FIG. 3 depicts the fastener fixating mesh to tissue.

Turning now to FIGS. 1, 2 and 3, depictions of the fastener of the current invention, generally designated as 10. Fastener 10 comprises three sections, head section 11, mesh retention section 12, and threaded tissue-snaring section 13. Head section 11 comprises two opposing head threads 17 and two opposing open or slotted sections 16. The distal surface of head section 11 is formed onto the proximal end of mesh retention section 12. The preferred maximum dimension of head 11 transverse to the longitudinal axis of fastener 10 is 5 mm.

Mesh retention section 12 may, alternately, be tapered or right-cylinder shaped or may be omitted, which would allow the proximal end of threaded tissue-snaring section 13 to abut the distal end of head section 11. Unlike the embodiment of fastener 10 with no mesh retention section 12, either the conical or cylindrical configuration mesh retention section 12 locks mesh 52 on to fastener 10 when mesh 52 is screwed past the proximal-most tissue-snaring thread 15c since there is no thread located in mesh retention section 12 that would allow mesh 52 to be unscrewed from fastener 10. Mesh retention section 12 is generally cylindrical or conical shaped with a dimension transverse to its longitudinal axis that is smaller than the transverse dimension of head 11 and the transverse dimension of proximal most tissue-snaring thread 15c. Preferably the dimension transverse to the mesh retention section 12 longitudinal axis is 1 and 1.5 mm and the dimension parallel to the longitudinal axis is preferably between 0.5 and 1.5 mm.

Threaded tissue-snaring section 13 comprises aggressive, auger-like threads peaks, 15a, 15b and 15c. Threads 13 spiral in either a right hand or left hand manner (here shown right hand) from the distal end of mesh retention section 12 to the distal surface 14 of fastener 10 with, preferably, three thread peaks 15a, 15b, and 15c and two thread roots 19 band 19a.

Figure 7A:
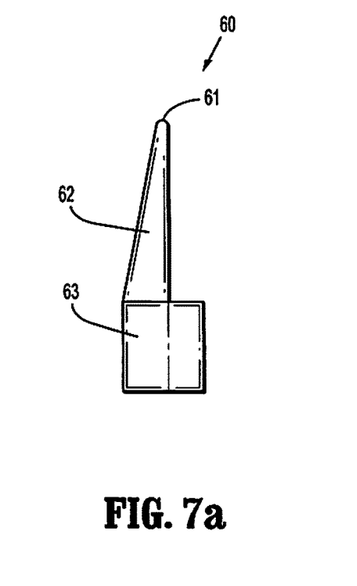
FIG. 7a is a side profile of fastener thread cutter.
Figure 7B:
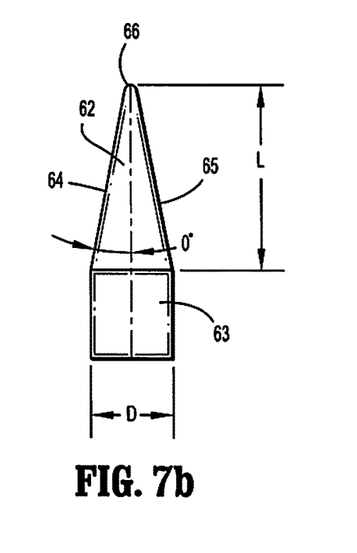
FIG. 7b is a front profile of fastener thread cutter.
Figure 8:
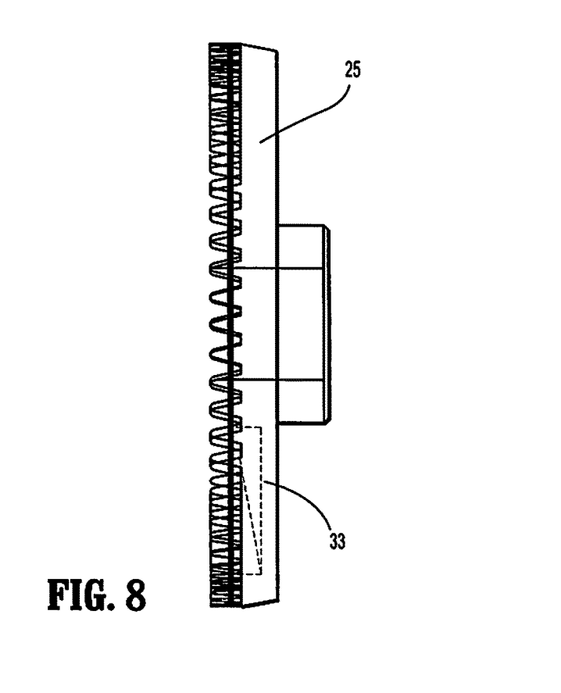
FIG. 8 depicts the side view of bevel gear with groove.

FIG. 8 depicts a preferred embodiment of a tool steel thread cutter 60 for cutting thread section 13. Cutter 60 comprises a mounting shank 63 of diameter D and cutter section 62. Tapering a length of cylinder with angle theta and then removing half the tapered material to the centerline of the cylinder as depicted in FIGS. 7a and 7b results in forming cutting section 62. Radii 61 and 66 preferably are ground on the tip of cutter section 62. Preferably, theta is 20 degrees, D is 4.8 mm, L is 5.8 mm and radii 61 and 63 are 0.5 mm.

Thread section 13 can be formed by securing, preferably, a cylinder of absorbable polymer material, 5 mm diameter in diameter to one rotating axis of a three-axis machine center. Cutter 60 is chucked into a spindle and rotated at a speed appropriate for cutting the material on to which thread section 13 is to be cut. The longitudinal axis of cutter 60 is perpendicular to the longitudinal axis of the cylinder. The distal tip of cutter 60 is initially positioned on the centerline of the cylinder at a distance X from the distal surface of the cylinder. The machine center is then programmed to translate cutter 60 away from the cylinder's axis, which is rotated about the longitudinal axis, and simultaneous to move the cutter proximal. By starting the cutter distal of the cylinder, but on the centerline, the auger-type thread section 13 are formed. Any partial threads that occupy the mesh retention section 12 are then milled out so that mesh retention section 12 is preferably circular in cross section. Preferably, X is set to 0.75 mm and the machine center axis parallel to the cylinder axis is translated at a rate five times the rate at which cutter 60 is translated perpendicular to the cylinder axis. Preferably the cylinder is rotated four revolutions as cutter 60 moves from the starting position to just short of the distal surface of head 11. This process forms threads as depicted in FIG. 1. A similar, but mirrored process, can be employed to form electrodes for burning a cavity into each half of an injection mold. Care must be taken to insure surface 14 is sharp to insure fastener 10 easily penetrates tough mesh material such as expanded PTFE. Fastener 10 is then completed by cutting the partial head threads 17 using process well known in the art.

First thread peak 15c is formed at the distal end of mesh retention section 12 and is smaller in dimensions transverse to the longitudinal axis than head section 11 and larger than mesh retention section 12 in dimensions transverse to the axis. The preferred transverse dimensions are 3.7 mm and 1.1 mm of the first thread peak 15c and the first root 19b respectively. The preferred transverse dimensions for second thread peak 15b and second thread root 19a are 2.9 mm and 0.4 mm respectively. The preferred transverse dimension of third thread peak 15a is 1.5 mm.

Distal surface 14 is the terminus of tissue-snaring section 13. Owing to the process described above threads 18 terminate distally prior to reaching an apex. The dimension D shown in FIG. 1 is the transverse dimension of the distal most thread 15a of threaded tissue-snaring section 13. D should be as large as design constraints will allow, preferably, greater than 1 mm. This geometry allows for ease of mesh penetration and minimizes indentation of the mesh into soft tissue as compared to a pointed distal end. A larger value of D, results in less pressure to cause indentation of tissue 51 and mesh 52, for a given distal force exerted on applier 20 by the surgeon.

Figure 4:
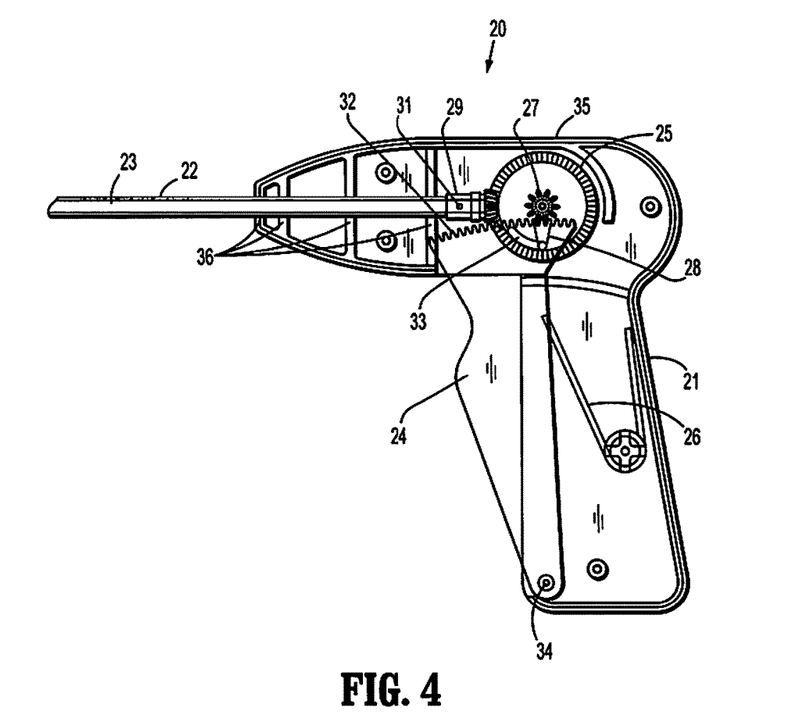
FIG. 4 is a cutaway view of the proximal end of the applier according to the present invention.
Figure 5:
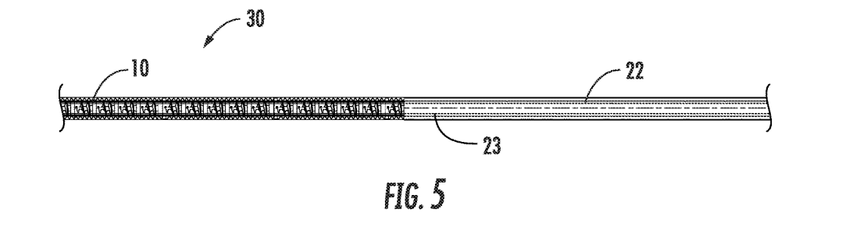
FIG. 5 is a cutaway view of the distal end of the applier according to the present invention.
Figure 6:
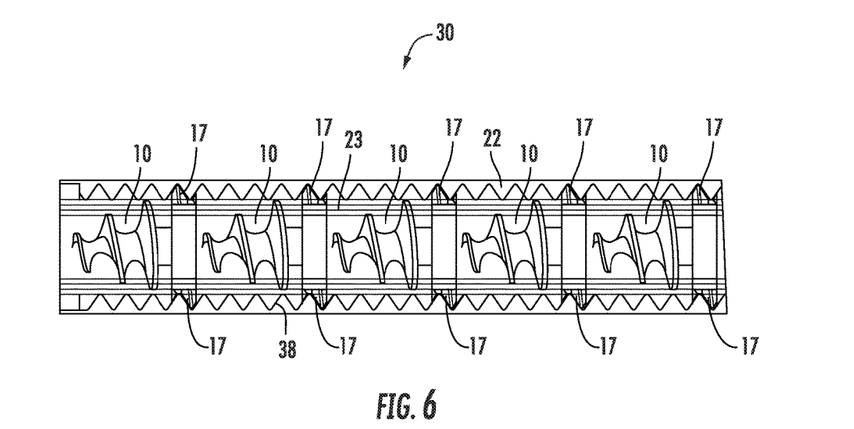
FIG. 6 is an enlargement of a cutaway view of the distal end of the applier according to the present invention.

Turning now to FIGS. 4, 5, and 6 depicting the delivery device, or applier, for mesh fastener 10, generally designated as 20. FIG. 4 is a cutaway view of the proximal end or body 35 of applier 20. Body 35 of applier 20 comprises handle 21, outer tube 22 stabilizer ribs 36, inner tube 23, trigger 24 with trigger gear 32 and trigger pivot 34 attached to handle 21, bevel gear 25, return spring 26, pinion gear 27, anti reversal drive 28, and bevel pinion gear 29. Pivot 34 is fixedly mounted to handle section 21 of body 35 and the axial for pinion 27 and bevel 25 is fixedly mounted to body 35. Drive 28 is fixed to pinion 27 owing to spline hub 36 that is fixedly attached to pinion 27. Drive 28 rotates bevel 25 owing to drive tooth 41 depicted in FIG. 9 mating into groove 33 in bevel 25 shown in FIG. 8.

FIG. 5 depicts the distal end 30 of applier 20 with twenty fasteners 10 loaded, ready for use.

FIG. 6 is cutaway view of an enlargement of the distal end 30 of applier 20 depicting the distal most five fasteners 10. Head threads 17 of fasteners 10 engage internal screw threads 38 in outer tube 22. The distal end of inner tube 23 is slotted to accept multiple fasteners 10, having two tines opposite the two slots, not shown because of the cutaway, that engage two fastener slots 16. Head threads 17 extend between the tines to engage outer tube threads 38. Rotation of inner tube 23 about its longitudinal axis rotates fasteners 10 and advances them distally owing to head threads 17 engagement with outer tube threads 38. In the preferred embodiment fasteners 10 are not in forced engagement with each other to avoid damage to distal tip 14 of fasteners 10.

In a preferred embodiment there are twenty-four tube threads 38 per inch, the overall length of fastener 10 is 0.203 inches, with five full turns of inner tube 23 advancing fasteners 10 0.208 inches. The distal end of outer tube 22 comprises counter bored 39 that preferably has a depth of 0.030 inches, which allows distal most fastener 10 to release from outer tube threads 38 in the last three quarters of a turn of a five turn actuation sequence in the application and ejection process, as will be detailed below.

Five embodiments of fastener 10 are described herein comprising four different molar ratios of DLPL and PG. The resins of the co-polymers in each case were prepared using well-known techniques of polymerization of cyclic dimers. The molar percentages (M) of DLPL and PG were measured along with the residual monomer percentage (RM). After polymerization the resins were thoroughly dried. Fastener 10 was then injection molded in a standard micro-molding machine at 150 Deg. C. The transition glass temperature (Tg), the absorption time at 37 Deg. C. (to 20% of the original mass) (AT), the tensile strength (TS) and Young's modulus (YM) were then measured. Fastener 10 was then subjected to 25 kgy E Beam radiation and the tensile strength and Young's modulus re-measured. Standard techniques, well known by those skilled in the art, were employed in the measurements of each of the parameters. The results are shown below:

| | | | | Case I | | | |
| --- | --- | --- | --- | --- | --- | --- | --- |
| Parameter | M, DLPL, % | M, PG, % | RM, % | Tg, Deg. C. | AT, Months | TS, PS | YN, PSI |
| | 100 | 0 | 2.1 | 49.4 | 13 | 6100 | 206,000 |

| | | | | Case II | | | |
| --- | --- | --- | --- | --- | --- | --- | --- |
| Parameter | M, DLPL, % | M, PG, % | RM, % | Tg, Deg. C. | AT, Months | TS, PS | YN, PSI |
| | 85 | 15 | 2.1 | 49.7 | 5.8 | 7900 | 198,000 |

| | | | | Case III | | | |
| --- | --- | --- | --- | --- | --- | --- | --- |
| Parameter | M, DLPL, % | M, PG, % | RM, % | Tg, Deg. C. | AT, Months | TS, PS | YN, PSI |
| | 75 | 25 | 1.6 | 49.1 | 4.3 | 7200 | 192,000 |

| | | | | Case IV | | | |
| --- | --- | --- | --- | --- | --- | --- | --- |
| Parameter | M, DLPL, % | M, PG, % | RM, % | Tg, Deg. C. | AT, Months | TS, PS | YN, PSI |
| | 65 | 35 | 1.9 | 47.2 | 3.2 | 7400 | 190,000 |

| | | | | Case V | | | |
| --- | --- | --- | --- | --- | --- | --- | --- |
| Parameter | M, DLPL, % | M, PG, % | RM, % | Tg, Deg. C. | AT, Months | TS, PS | YN, PSI |
| | 52 | 48 | 1.2 | 46.7 | 1.5 | 8100 | 188,000 |

In each case retesting the tensile strength and Young's modulus after subjecting the fastener 10 to 25 kgy E Beam radiation yielded results statistically indistinguishable from the values in the tables above.

To design an appropriate insulated shipping container the historical average daily temperatures over a "hot weather route" from Florida to Arizona were obtained from www.engr.udayton.edu/weather. Heat flux data were determined from the historical data resulting in an insulation requirement of 2.5 inches of Cellofoam (a registered trademark of Cellofoam of North America, Inc.) with a thermal R-value of 3.86 per inch of thickness. Fasteners 10 were then shipped over the route packed in the insulated container and the internal temperature of a un-air conditioned cargo space of a roadway common carrier was measured during a five-day trip from Jacksonville Fla. to Phoenix Ariz. from Sep. 9 till Sep. 14, 2004. The internal temperatures of the cargo space, Tc, and the internal temperature of the insulated container, Ti, containing fasteners 10 were recorded every 30 minutes. The minimum and maximum temperatures in the cargo space and the insulated container are shown below:

|  | Day 1 | Day 2 | Day 3 | Day 4 | Day 5 |
| --- | --- | --- | --- | --- | --- |
| Maximum Tc Deg. C. | 37 | 34 | 29 | 48 | 50 |
| Minimum Tc Deg. C. | 24 | 18 | 15 | 27 | 27 |
| Maximum Ti Temperature Deg. C. | 27 | 27 | 26 | 27 | 27 |
| Minimum Ti Temperature Deg. C. | 24 | 26 | 21 | 24 | 24 |

Thus it is seen from the data above that the insulated shipping container is adequate for maintaining fastener 10 temperatures well below the glass transition temperature of 49 Deg. C. of the preferred co-polymer, 75/25 DLPL/PG, Case III above.

The preferred embodiment for the current invention is an injection molded fastener as depicted in FIG. 1 comprising 75% DLPL, 25% PG, sterilized with radiation, either gamma or E Beam, at 25 kgy and packaged first in a hermetically sealed pack and an insulated shipping container.

Applier Loading and Operation

Multiple fasteners 10 are loaded onto the tines of inner tube 23 head to tail with distal end 14 pointed distally. Fasteners 10 are rotationally orientated such that the tines of inner tube 23 engage head slots 16. The proximal end of the loaded inner tube assembly is inserted into the distal end of outer tube 22 until proximal-most fastener 10 encounters outer tube threads 38. The inner tube assembly is then rotated until the distal end of inner tube 23 is flush with or slightly recessed into outer tube 22. In this position the proximal end of inner tube 23 is proximal of the proximal end of outer tube 22. Near the proximal end of inner tube 23 a drill through hole perpendicular to the longitudinal axis is located to accept bevel pinion pin 31 for securing bevel pinion 29 to inner tube 23. The inner and outer tube assembly is then affixed into handle 21 with ribs 36 locking outer tube 22 against rotation or twisting in body 35. Two clamshell halves are ultrasonic welded or otherwise fastened together to form body 35.

Following sterilization loaded applier 20 is placed into a surgical field, usually through a 5 mm trocar, and the distal end of applier 20 is held firmly against mesh 52, which covers tissue 51. Outer tube threads 38 act as a force reactor to counter the distal force, generated by the screw-in process of the threaded tissue-snaring section 13, so that fasteners 10 are unable to move proximally. Outer tube threads 38 engaging head threads 17 also restrain fasteners 10 from falling out of the distal end of applier 20 under the influence of gravity, for example.

Trigger 24 is then rotated clockwise about pivot 34 causing pinion 27 to rotate counterclockwise. Drive tooth 41 is engaged in groove 33 and thus rotates bevel 25 counter-clockwise. Bevel 25 causes bevel pinion 29 to rotate clockwise (in right hand sense, conventionally). The gear train is sized such that full movement of trigger 24 gear teeth 32 causes 5 revolutions of bevel pinion 29 and hence 5 revolutions of inner tube 23. This rotation of inner tube 23 rotates the stack of fasteners 10 five complete revolutions and advances them preferably 5.2 mm, the length of fastener 10, owing to head threads 17 and the pitch of outer tube threads 38, preferably 24 threads per inch.

Figure 9:
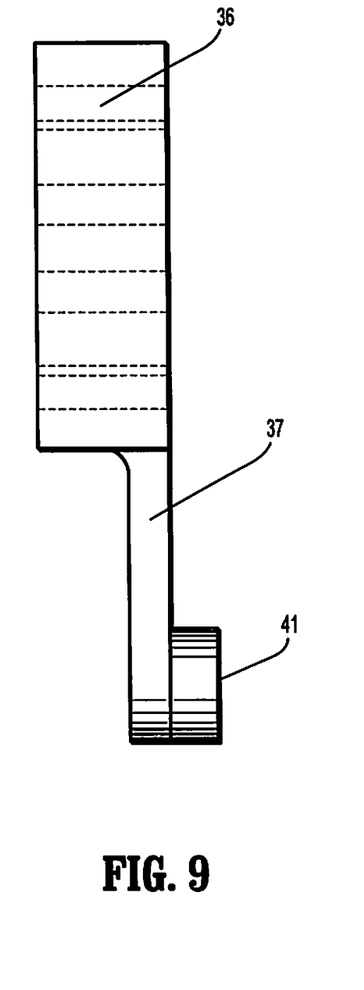
FIG. 9 is the anti-reversal drive device.

As explained above rotation of inner tube 23 rotates fasteners 10. Distal surface 14 of distal most-fastener 10 engages and penetrates mesh 52 and threaded tissue-snaring section 13 screws into and draws tissue 51 and mesh 52 together. During the last three quarters of a rotation of the five revolutions head threads 17 of distal most fastener 10 enter into counter bore 39. Removal of the distal end 30 of applier 20 from mesh 52 releases distal-most fastener 10 and ejects it from applier 20. Mesh 52 is thus affixed to tissue 51. After the fastener screw-in process is complete trigger 24 is released, reset spring 26 returns trigger 24 with trigger gear 32 to its start, or home, position. This rotates pinion 27 and drive 28 clockwise. Flexible arm 37 allows drive tooth 41 to ride up out of groove 33 and rotate about the face of bevel 25 without bevel 25 rotating owing to greater friction of bevel 25 against its axial. Thus bevel 25, bevel pinion 29, inner tube 23, and fasteners 10 do not rotate during the return stroke of applier 20 during the reset process leaving the stack of fasteners 10 forward with each remaining fastener moved distally one fastener length. The features of applier 20 describe herein assures that the plurality of fasteners 10 progress distally one fastener length and do not move proximal during the return stroke. At the end of the return stroke drive tooth 41 has rotated 360 degrees on the face of bevel 25 and it snaps back into groove 33 and in position to drive bevel 5. Applier 20 is fully reset and ready for the deployment of the next fastener 10.

From the foregoing, it will be appreciated that the absorbable fastener of the present invention functions to securely fasten tough, non macro-porous, and relative inelastic mesh to tissue. The fastener of the present invention will disintegrate after the body has secured the mesh against migration and contraction. The absorbable fastener of the present invention can be sterilized so that mechanical properties are maintained and it can be shipped under severe temperature conditions with insulated packaging so that the glass transition temperature is not exceeded. It will also be appreciated that the absorbable fastener of the present invention may be utilized in a number of applications such as hernia repair, bladder neck suspension, and implant drug delivery systems.

While several particular forms of the invention have been illustrated and described, it will be apparent by those skilled in the art that other modifications are within the scope and spirit of the present disclosure.

What is claimed is:

1. A fastener applier apparatus comprising:
   a body;
   a trigger supported on the body;
   an outer tube extending from the body;
   at least one non-cannulated threaded fastener configured to threadably engage the outer tube;
   a pinion gear supported on the body and operatively connected to the trigger, wherein actuation of the trigger results in rotation of the pinion gear in a first direction and release of the trigger results in rotation of the pinion gear in a second direction opposite to the first direction; and a bevel gear supported on the body and operatively connected to the pinion gear, wherein rotation of the pinion gear in the first direction engages the bevel gear to rotate the bevel gear in the first direction, and wherein the bevel gear does not rotate as the pinion gear rotates in the second direction.

2. The fastener applier apparatus of claim 1, wherein one complete squeeze of the trigger results in one complete rotation of the bevel gear.

3. The fastener applier apparatus of claim 1, further including a drive tooth associated with the pinion gear, and wherein the bevel gear defines a groove formed in a surface thereof for selective receipt of the drive tooth therein.

4. The fastener applier apparatus of claim 3, wherein rotation of the pinion gear in the first direction causes the drive tooth to engage the groove of the bevel gear to enable the bevel gear to rotate in the first direction.

5. The fastener applier apparatus of claim 3, wherein rotation of the pinion gear in the second direction causes the drive tooth to disengage from the groove of the bevel gear and prevent the bevel gear from rotating in the second direction.

6. The fastener applier apparatus of claim 1, wherein the at least one non-cannulated threaded fastener includes a threaded head section and a distal tissue snaring section, the threaded head section threadably engaged with threads of the outer tube.

7. The fastener applier apparatus of claim 1, wherein the at least one non-cannulated threaded fastener distally advances through the outer tube in response to rotation of the pinion gear in the first direction.

8. The fastener applier apparatus of claim 1, further including a bevel pinion coupled to the bevel gear, the bevel pinion rotatable in response to rotation of the bevel gear.

9. The fastener applier apparatus of claim 8, further including an inner tube coupled to the bevel pinion and rotatable in response to rotation of the bevel pinion.

10. The fastener applier apparatus of claim 9, wherein the inner tube is configured to distally advance the at least one non-cannulated threaded fastener through the outer tube in response to rotation of the inner tube relative to the outer tube.

11. The fastener applier apparatus of claim 1, wherein the trigger is spring-biased toward an unactuated position by a return spring.

12. A fastener applier apparatus comprising:
a body;
an outer tube extending from the body;
at least one non-cannulated threaded fastener supported in the outer tube;
a trigger pivotably coupled to the body and including a trigger gear;
a pinion gear rotatably coupled to the trigger gear of the trigger;
a flexible drive tooth associated with the pinion gear; and
a bevel gear defining a groove formed in a surface thereof, the groove configured to engage the drive tooth as the pinion gear rotates in a first direction and disengage the drive tooth as the pinion gear rotates in a second direction, the trigger gear configured to rotate the pinion gear without rotating the bevel gear as the pinion gear rotates in the second direction.

13. The fastener applier apparatus of claim 12, wherein one complete squeeze of the trigger results in one complete rotation of the bevel gear.

14. The fastener applier apparatus of claim 12, wherein the drive tooth is coupled to a flexible arm that flexes to enable the drive tooth to selectively engage the groove as the pinion gear rotates between the first and second directions.

15. The fastener applier apparatus of claim 12, wherein the trigger includes a first end and a second end opposite to the first end, and wherein the body includes a handle, the first end of the trigger pivotably coupled to the handle of the body, the second end of the trigger having the trigger gear formed thereon.

16. The fastener applier apparatus of claim 12, wherein the trigger is spring-biased toward an unactuated position by a return spring.

17. The fastener applier apparatus of claim 12, further including a bevel pinion coupled to the bevel gear and an inner tube coupled to the bevel pinion, the bevel pinion and the inner tube rotatable in response to rotation of the bevel gear.

18. The fastener applier apparatus of claim 17, wherein the inner tube is configured to distally advance the at least one non-cannulated threaded fastener through the outer tube in response to rotation of the inner tube.

19. The fastener applier apparatus of claim 12, wherein the at least one non-cannulated threaded fastener includes a threaded head section and a distal tissue snaring section, the threaded head section threadably engaged with threads of the outer tube.

* * * * *